Figure 1:
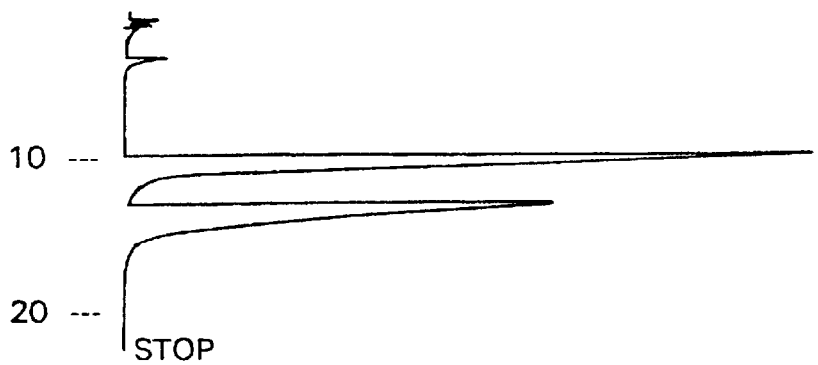

United States Patent [19]

Scheinmann et al.

[11] Patent Number: 6,143,933
[45] Date of Patent: Nov. 7, 2000

[54] PROCESS FOR THE PREPARATION OF OPTICALLY ACTIVE METHADONES IN HIGH ENANTIOMERIC PURITY

[75] Inventors: Feodor Scheinmann, Sale; Jonathan David Hull, Stockport; Nicholas John Turner, Edinburgh, all of United Kingdom

[73] Assignee: Salford Ultrafine Chemicals & Research Ltd., United Kingdom

[21] Appl. No.: 09/194,452

[22] PCT Filed: May 27, 1997

[86] PCT No.: PCT/GB97/01441

§ 371 Date: Apr. 9, 1999

§ 102(e) Date: Apr. 9, 1999

[87] PCT Pub. No.: WO97/45551

PCT Pub. Date: Dec. 4, 1997

[30] Foreign Application Priority Data

May 25, 1996 [GB] United Kingdom .................. 9611041

[51] Int. Cl.$^7$ .................................................. C07C 213/00
[52] U.S. Cl. ......................................... 564/318; 564/317
[58] Field of Search ..................................... 564/317, 318

[56] References Cited

PUBLICATIONS

Rudaz, S et al. J. Pharm. Biomed Anal (1996) 14 (8–10) 1271–1279.

Berthod, A et al. J. Pharm. Biomed Anal (1990) 8 (2) 123–30.

*Primary Examiner*—Paul J. Killos
*Attorney, Agent, or Firm*—Welsh & Katz, Ltd.

[57] ABSTRACT

A method of preparing optically active methadones comprises an enzymatic process for the resolution of 1-dialkyl-amino-2-propanol and conversion of the enantiomers to the optically active methadones in high enantiomeric purity.

11 Claims, 3 Drawing Sheets

Racemic methadone (Sigma)

START
96/02/02    15:01:51

CHROMATOGRAM 13 MEMORIZED

| PKNO | TIME | AREA | MK | IDNO | CONC | NAME |
|---|---|---|---|---|---|---|
| 1 | 3.328 | 66585 | S | | 0.9568 | |
| 2 | 10.05 | 3449348 | | | 49.5673 | |
| 3 | 13.133 | 3442983 | V | | 49.4758 | |
| TOTAL | | 6958915 | | | 100 | |

R-(-)-methadone

START
96/02/02          15:54:59

CHROMATOGRAM 15 MEMORIZED

| PKNO | TIME | AREA | MK | IDNO | CONC | NAME |
|---|---|---|---|---|---|---|
| 1 | 9.7 | 10392024 | V | | 99.8456 | |
| 2 | 14.177 | 16073 | | | 0.1544 | |
| | TOTAL | 10408096 | | | 100 | |

S-(+)-methadone

| PKNO | TIME | AREA | MK | IDNO | CONC | NAME |
|---|---|---|---|---|---|---|
| 1 | 10.49 | 10185 | | | 0.1159 | |
| 2 | 12.55 | 8780478 | | | 99.8841 | |
| TOTAL | | 8790663 | | | 100 | |

PROCESS FOR THE PREPARATION OF OPTICALLY ACTIVE METHADONES IN HIGH ENANTIOMERIC PURITY

This invention relates to a process for the preparation of optically active methadones and in particular to an enzymatic process for the resolution of 1-dialkyl-amino-2-propanol and conversion of the enantiomers to the optically active methadones in high enantiomeric purity.

Racemic methadone is an analgesic and is used to ease heroin withdrawal. The levo-isomer of methadone has been reported to possess greater physiological activity than the racemic modification (A. A. Larsen, B. F. Tullar, B. Elpern and J. S. Buck, *J. Amer. Chem. Soc.*, 1948, 70, 4194.) Previous methods for preparing optically active methadones involved resolution of racemic methadone itself or its nitrile precursor by preparing diastereomeric salts with d-tartaric acid (A. A. Larsen, B. F. Tullar, B. Elpern and J. S. Buck, *J. Amer. Chem. Soc.*, 1948, 70, 4194.) (W. R. Brode and M. W. Hill, *J. Org. Chem.*, 1948, 13, 191.) or (+)-3-bromocamphor-8-sulphonic acid ammonium salt (E. E. Howe and M. Sletzinger, *J. Amer. Chem. Soc.*, 1949, 71, 2935.) The dextro-isomer of methadone can be synthesised from ethyl L-(−)-lactate involving the intermediates in scheme 2 hereinafter (C. J. Barnett and J. C. Smirz, *J. Org. Chem.*, 1976, 41, 710.).

The present invention seeks to provide an alternative more economical method for preparing optically active methadones.

According to the present invention there is provided a method of preparing optically active methadones comprising the enzymatic resolution of 1-dialkylamino-2-propanol in the presence of ester so as to produce S-1-dialkylamino-2-propanol and R-ester of 1-dialkylamino-2-propanol, the method further comprising the conversion of one or both of the S-1-dialkylamino-2-propanol and/or R-ester of 1-dialkylamino-2-propanol to yield S(+)-methadone and/or R(−)-methadone respectively.

Preferably 1-Dimethylamino-2-propanol is used as the starting material.

The process of the invention involves the enzymatic resolution of racemic 1-dialkyl amino-2-propanol which is a cheap starting material to provide R- and S-enantiomers. These enantiomers can be converted into the optically active methadones in high enantiomeric excess. Advantageously, the resolved alcohol and esters allow conversion, without loss of optical activity, to R(−)- and S(+)-methadones in high enantiomeric purity, as demonstrated by HPLC methods using a chiral stationary phase. (±)-1-dimethylamino-2-propanol may be resolved into its optical isomers by an enzyme, preferably lipase, catalysed transesterification using various esters and enzymes either as crude preparations or purified enzymes immobilised on solid support. The effective enzymes have included the following:

Pseudomonas cepacia (Amano lipase PS)
Aspergillus niger (Lipase A "Amano" 6)
Candida rugosa (Amano lipase AY)
Mucor javanicus (Lipase M "Amano" 10)
Penicillium camembertii (Lipase M "Amano" 50)
Rhizopus niveus (Amano Lipase N conc.)
Candida antartica (Novozym® 435)
Pig Liver Esterase (Sigma)
Porcine Pancreatic Lipase (Sigma)

Preferred esters include vinyl acetate and vinyl propionate. The process can be illustrated with the use of a vinyl propionate as the acyl donor and *Candida antartica* (Novozym® 435) as the immobilised enzyme. This process gives the R-ester and the S-alcohol. The R-ester can be isolated simply by extraction or alternatively by a distillation process which gives both the ester and the alcohol in good yields. The resolution is illustrated in scheme 1 shown below.

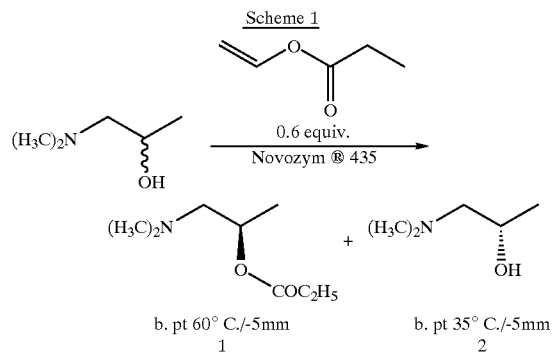

Scheme 1

For high enantiomeric excess in formation of the propionate ester 0.5 equivalents of vinyl propionate were used. For high optical purity of the S-alcohol approximately 0.6 equivalents of vinyl propionate were used so that all the R-alcohol would be esterified as well as a small amount of S-alcohol. The remaining S-alcohol has high optical purity.

The alcohol 2 is the first fraction to distil (35° C./−5 mm) followed by a small amount of mixed 1 & 2 and then the propanoate ester 1 (60° C./−5 mm). The resolved S-alcohol ($[\alpha]_D$=23°,lit (C. J. Barnett and J. C. Smirz, *J. Org. Chem.*, 1976, 41, 710.)=24°) was then treated with thionyl chloride to afford the chloro compound 3. This was converted to S-(+)-2,2-diphenyl-4-dimethylaminopentane-nitrile 5a by reaction with diphenylacetonitrile in the presence of strong base (C. J. Barnett and J. C. Smirz, *J. org. Chem.*, 1976, 41, 710.), M. Bockmühl and G. Ehrhart, *Liebigs Annalen Chem.*, 1949, 561, 52.), J. H. Poupaert et al., *J. Chem. Research* (S), 1981, 192). Grignard reaction of 5a with ethyl magnesium-bromide followed by acid hydrolysis gave S-(+)-methadone 5b in good yield (Scheme 2 below) (J. H. Poupaert et al, *J. Chem. Research (S)*, 1981, 192.). Phase transfer catalysts for the conversion of the chloro compound 3 to the nitrile 5a improved the regioselectivity of the attack on the aziridinium ion intermediate 4. Selectivity was observed using dibenzo-18-crown-6 (J. H. Poupaert et al, *J. Chem. Research (S)*, 1981, 192.), 18-crown-6, and tris[2-(2-methoxyethoxy)ethyl]amine which gave 5 in preference to 6. The chiral ester 1 was converted using a similar sequence of reactions to R-(−)-methadone 9b (scheme 3 below).

S-(+) Methadone may be converted to the analgesic, levo-acetylmethadol (LAAM) by conventional methods (E. L. May and E. Mosettig, *J. Org. Chem*, 1948, 13,459 and M. E. Speete, W. M. Byrd, L. C. Cheney and S.B. Binkley, *J. Am. Chem. Soc.*, 1949, 71, 57).

Scheme 2

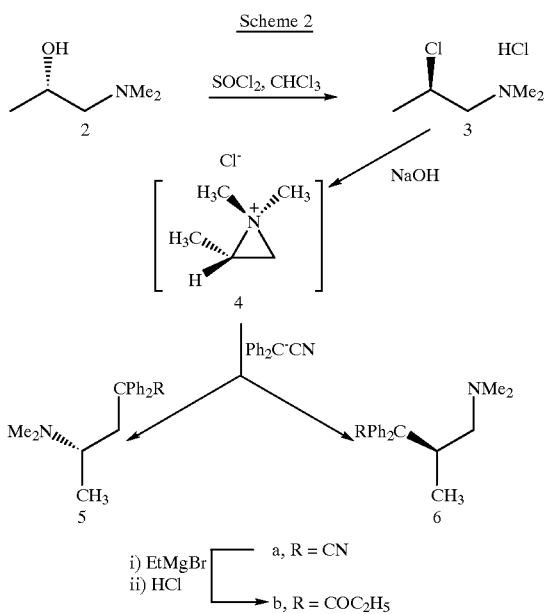

a, R = CN
b, R = COC$_2$H$_5$ i) EtMgBr
ii) HCl

Scheme 3

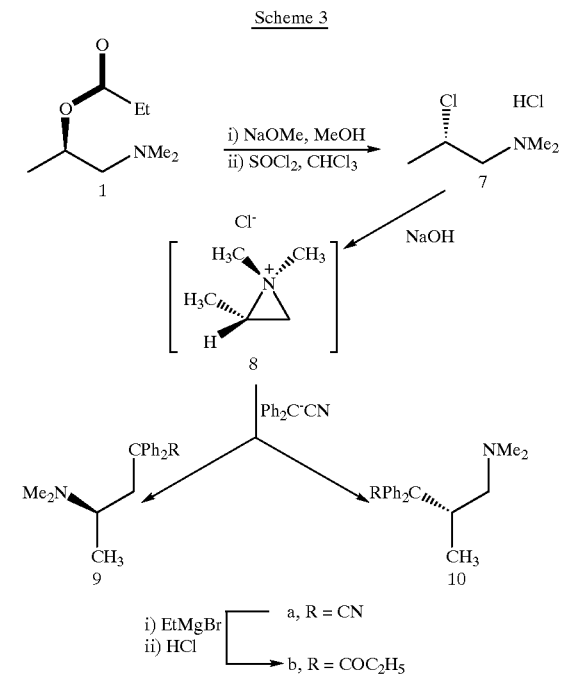

a, R = CN
b, R = COC$_2$H$_5$ i) EtMgBr
ii) HCl

The literature data quoted for optical rotations of the chiral methadones varied considerably and it was necessary to provide alternative data for optical purity (A. A. Larsen, B. F. Tullar, B. Elpern and J. S. Buck, *J. Amer. Chem. Soc.*, 1948, 70, 4194.) (E. E. Howe and M. Sletzinger, *J. Amer. Chem. Soc.*, 1949, 71, 2935.) (The Merck Index 11th Edn, Merck and Co., Inc. (1989). Both isomers were analysed for optical purity by chiral HPLC using a Chiral-AGP column.

Figure 2:
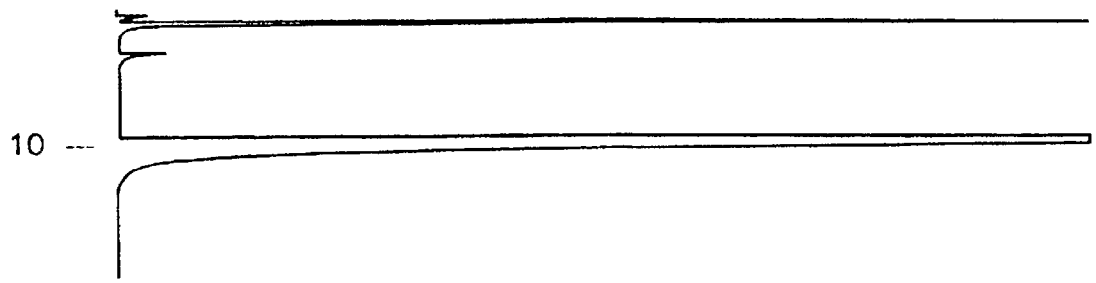
Figure 3:
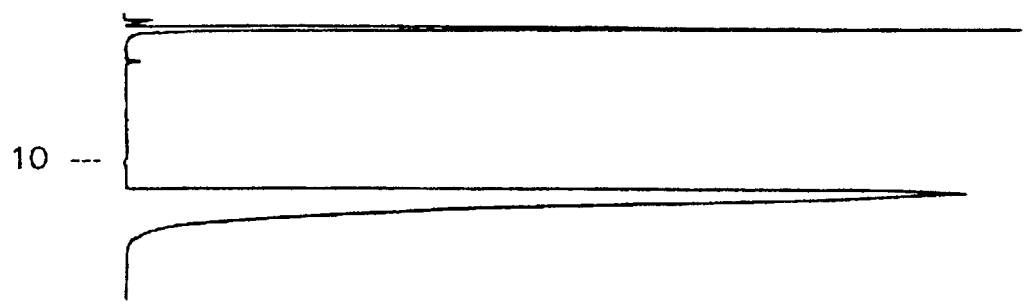

FIGS. 1 to 3 show high pressure liquid chromatograms for conventional racemic methadone (FIG. 1) and for R-(−) methadone (FIG. 2) and s-(+)methadone (FIG. 3) made in accordance with the process of the invention.

The first trace is of racemic methadone and shows excellent separation and the same peak area for each enantiomer. The two traces for S- and R-methadone show no evidence of the optical antipode and enantiomeric excess in each case is greater than 99%. The HPLC operating conditions are set out below.

Chiral HPLC conditions:
Column—Chiral-AGP 100×4 mm+guard 10×3 mm
Mobile Phase—840:160 0.01M sodium phosphate buffer pH 6.50/Acetonitrile
Flow Rate—0.9 ml/min
Solution—1 mg in 8 ml of mobile phase
Injection volume—20 µl
Detector—20 nm In order that the present invention may be more readily understood specific embodiments thereof will now be described by way of illustration only.

Melting Points were determined on a Reichert-Jung micro hot stage apparatus and are uncorrected. Optical rotations were measured on an Optical Activity polAAr 2001 Polarimeter having a readability of ±0.001°, using a 1 dm tube. $^1$H NMR were obtained on a Perkin Elmer R34 220 MHz instrument with tetramethysilane as internal standard. Infrared spectra were carried out on a Perkin Elmer 1310 spectrophotometer. Chiral HPLC was run on a chiral-AGP column supplied by ChromTech AB, Norsborg, Sweden.

PART 1

R-(−)-methadone

Resolution of 1-dimethylamino-2-propanol

R-(−)-1-dimethylamino-2-propyl propanoate, 1

Racemic 1-dimethylamino-2-propanol (100 g, 0.97 mol) was stirred with vinyl propionate (106 ml, 0.97 mol) at ambient temperature and Novozym 435 (6 g) was added. The reaction mixture was stirred slowly for 70 hours and after this time tlc (10% methanol/dichloromethane—visualise KMnO$_4$ solution) indicated that the reaction had gone to 50% conversion. The enzyme was removed by filtration and the filter bed was washed with ethyl acetate (2×100 ml). The organic layer was then washed with water (4×100 ml) and the combined washes were back extracted with ethyl acetate (400 ml). The organic layer was then washed with brine (200 ml) and dried (MgSO$_4$). The ethyl acetate was removed in vacuo to leave 58.7 g (0.37 mol, 70% based on maximum yield of 84.5 g) of (−)-1-dimethylamino-2-propyl propanoate as a yellow oil. $\delta_H$ (220 MHz; CDCl$_3$) 1.13 (3H, t, 7 Hz, CH$_3$CH$_2$CO), 1.21 (3H, d, 6 Hz, H-3), 2.25 (6H, s, N(CH$_3$)$_2$), 2.10–2.60 (4H, m, H-1 & CH$_3$CH$_2$CO), 5.09 (1H, m, H-2). The optical purity was not measured at this stage.

R-(−)-1-dimethylamino-2-propanol

A solution of sodium methoxide was made up by dropping small pieces of sodium metal (200 mg) into methanol (5 ml) under a blanket of argon. This was then added to a stirred solution of (−)-1-dimethylamino-2-propyl propanoate (57.7 g, 0.36 mol) in methanol (200 ml). The mixture was stirred overnight and checked for completion by tlc (10% methanol/dichloromethane). The methanol was removed under reduced pressure and the crude R-(−)-1-dimethylamino-2-propanol (32.8 g, 88%) was analysed by 220 MHz NMR. $\delta_H$ (220 MHz; CDCl$_3$) 1.15 (3H, d, 6 Hz, H-3), 2.25 (6H, s, N(CH$_3$)$_2$) 2.10–2.50 (2H, m, H-1), 3.50 (CH$_3$OH), 3.85 (1H, m, H-2), 7.40 (CHCl$_3$).

S-(+)-1-dimethylamino-2-chloropropane Hydrochloride, 7

A solution of thionyl chloride (37 ml, 0.48 mol) in chloroform (20 ml) was added slowly, with stirring, to a cooled (ice/water) solution of R-(−)-1-dimethylamino-2-propanol (31.8 g, 0.32 mol) in chloroform (85 ml). When the addition was complete a precipitate formed. The mixture was allowed to warm to room temperature over 30 minutes and then heated to reflux for a further 30 minutes. The precipitate redissolved on heating but then the product crystallised out from the boiling solvent as it formed. More chloroform (20 ml) was needed to maintain the stirring. The cooled mixture was diluted with ether and filtered. The crude product (45.2 g, 89%) was recrystallised from 2-propanol and decolourising charcoal was used. The product (33.1 g, 65%) was obtained in 3 crops and the first crop (24.5 g) was kept separate; $[\alpha]_D$+59.1° (c 2.075, H$_2$O). This material was recrystallised twice more to give 15.7 g, 31% of S-(+)-1-dimethylamino-2-chloropropane hydrochloride, mp 192–193°, $[\alpha]_D$+65.9° (c 2.01, H$_2$O) [lit. (C. J. Barnett and J. C. Smirz, *J. Org. Chem.*, 1976, 41, 710.) mp 192–193°, $[\alpha]_D$+65°], $\delta_H$ (220 MHz; D$_2$O) 1.60 (3H, d, 6 Hz, H-3), 3.00 (6H, s, N(CH$_3$)$_2$), 3.50 (2H, d, 7 Hz, H-1), 4.55 (1H, m, H-2), 4.80 (HOD).

R-(−)-2,2-diphenyl-4-dimethylaminopentanenitrile, 9a

A 50% w/v solution of sodium hydroxide in water (12.5 ml, 0.32 mol) was added to a mechanically stirred suspension of diphenylacetonitrile (15.0 g,0.08 mol) and dibenzo-18-crown-6 (0.5 g, cat.) in dimethylsulphoxide (12.5 ml). The colour rapidly deepened to an orange/brown. S-(+)-1-dimethylamino-2-chloropropane hydrochloride, 7 (15 g, 0.095 mol) was added in portions over 30 minutes, this caused the temperature to rise to 30° C. After the addition was complete the mixture was warmed to 45–50° C. (water bath) and stirred for a further hour. The reaction mixture was then allowed to cool to room temperature and was poured into ice/water (250 ml) and extracted with ethyl acetate (3×150 ml). The combined extracts were dried (MgSO$_4$) and filtered and evaporated down to −100 ml. The product was extracted into 1N HCl (100 ml+50 ml) and this was back washed with ethyl acetate. The aqueous was basified with 2M sodium hydroxide and extracted into ethyl acetate (3×100 ml). The extracts were washed with brine (70 ml), dried (MgSO$_4$), and evaporated down to a yellow oil. This was chilled and triturated with cold hexane (−50 ml) to give a white solid which was collected by filtration and washed thoroughly with a further portion of cold hexane (100 ml). The solid was recrystallised from hexane to yield 7.0 g (32%) of 9a, mp 100–101° C., $[\alpha]_D$−50.2° (c 0.71, EtOH) [lit. (C. J. Barnett and J. C. Smirz, *J. Org. Chem.*, 1976, 41, 710.) mp 100–101°, $[\alpha]_D$−49°], $\delta_H$ (220 MHz; CDCl$_3$) 0.90 (3H, d, 6 Hz, H-5) 2.10 (6H, s, N(CH$_3$)$_2$) 2.20 (1H, dd, 12 & 5 Hz, H-3) 2.52 (1H, q, 5 Hz, H-4) 2.65 (1H, dd, 12 & 5 Hz, H-3) 7.3–7.5 (10 H, m, Ph$_2$CCN).

R-(−)methadone, 9b

All apparatus was dried and the reaction was carried out under an inert atmosphere of argon. A solution of R-(−)-2,2-diphenyl-4-dimethylaminopentanenitrile 9a (5.0 g, 0.018 mol) in toluene (15 ml) was added to a stirred solution of 3M ethyl magnesiumbromide in ether (10.7 ml, 0.03 mol). The ether was removed under reduced pressure and the remaining solution heated at reflux (135–140°) for 3 hours. The solution went slightly cloudy but there was no significant precipitation. After cooling to room temperature 2N HCl (30 ml) was added with care and then stirring was continued at 135–140° for a further 30 minutes. The two phases were allowed to separate and cool to room temperature. After scratching the sides of the flask a solid started to crystallise from the aqueous phase. The flask was cooled to complete crystallisation and the white solid was collected by filtration. This solid was recrystallised from water to yield 2.7 g (43%) of R-(−)-methadone. HCl. 9b (6-dimethylamino-4,4-diphenyl-3-heptanone hydrochloride), mp 242–244°, $[\alpha]_D$−136° (c 2.04, EtOH)[lit (The Merck Index 11th Edn, Merck and Co., Inc (1989) mp 241°, $[\alpha]_D$−145°], $\delta_H$ (220 MHz;d$^6$DMSO) 0.95 (3H, d, 6 Hz, H-7) 1.25 (3H, t, 7 Hz, H-1) 2.5–3.7 (11H, m, N(CH$_3$)$_2$ & H-6 & H-7 & H-2) 7.7–8.1 (10H, Ph$_2$C-4), I.R. (nujol,cm$^{-1}$) v=2400, 1700. Chiral HPLC shows no evidence of S-isomer—ee>99%.

PART 2

S-(+)-methadone

Resolution of 1-dimethylamino-2-propanol

S-(+)-1-dimethylamimo-2-propanol

Racemic 1-dimethylamino-2-propanol (100 g, 0.97 mol) was stirred with vinyl propionate (63.6 ml, 0.58 mol) at 40° C. and Novozym® 435 (5 g) was added. The reaction was stirred slowly for 75 hours and after this time tlc (10% methanol/dichloromethane—visualise KMnO$_4$ solution) indicated that the reaction had gone to at least 50% conversion. The enzyme was removed by filtration and the filtrate was distilled at reduced pressure. S-(+)-1-dimethylamino-2-propanol 2 was obtained as a colourless oil (31.6 g, 64%) bpt 35°/−5 mm, $[\alpha]_D$+23° (c 2.10, EtOH)[lit. (C. J. Barnett and J. C. Smirz, *J. Org. Chem. Soc.*, 1976 41, 710.) $[\alpha]_D$+24°], NMR-data as R-isomer.

R-(−)-1-dimethylamino-2-chloropropane

This was prepared following the same procedure as the S-isomer, 30.6 g of 2 were used and 45.0 g (96%) of crude product was isolated. This was recrystallised from 2-propanol as in the other series to give 30.9 g (65%) of 3, mp 192–193°, $[\alpha]_D$−65.8°[lit. (C. J. Barnett and J. C. Smirz, *J. Org. Chem.*, 1976, 41, 710.) mp 192–193°, $[\alpha]_D$−65°], NMR data as S-isomer.

S-(+)-2,2-diphenyl-4-dimethylaminopentanenitrile

This was prepared following the same procedure as the R-isomer. 30 g of 3 were used and 14.65 g (33%) of S-(+)-2,2-diphenyl-4-dimethylaminopentanenitrile 5a were obtained, mp 100–101° C., $[\alpha]_D$+52.9° (c 0.66, EtOH) [lit. C. J. Barnett and J. C. Smirz, *J. Org. Chem.*, 1976, 41, 710.) mp 100–101°, $[\alpha]_D$+49°], NMR—data as R-isomer.

S-(+)methadone

This was prepared following the same procedure as the R-isomer. 10 g of 5a were used and 6.6 g (53%) of S-(+)methadone. HCl 5b were obtained, mp 240–241° C., $[\alpha]_D$+136° (c 2.02, EtOH) [lit. (The Merck Index 11th Edn, Merck and Co., Inc. (1989) mp 241°, $[\alpha]_D$+145°]. NMR as R-isomer. Chiral HPLC shows no evidence of R-isomer, ee>99%.

6-Dimethylamino-4,4-diphenyl-3-heptanol

S-(+)-Methadone. HCl,5b (600 mg,1.74 mmol) was dissolved in ethanol (10 ml) and the solution was stirred whilst sodium borohydride (3.47 mmol) was added portionwise over a period of 5 minutes. When the addition was complete a spatula end of cerium (III) chloride heptahydrate was added. The resultant solution was allowed to stir at room temperature for 30 minutes then the ethanol was removed under reduced pressure. The residue was portioned between diethyl ether (40 ml) and water (40 ml). The aqueous layer was extracted with more diethyl ether (2×20 ml) and then the combined organics were washed with brine (40 ml) and dried (MgSO$_4$). The ether was removed under reduced pressure to leave 435 mg, 80% of 6-dimethylamino-4,4-diphenyl-3-heptanol.$\delta_H$ (220 MHz; CDCl$_3$) 0.8 (6H, d & t, 7 Hz, H-1 & H-7) 1.1 (1H,m,H-2) 1.75 (1H,m,H-2) 1.9–2.3 (2H,m,H-5) 2.15)6H,s,N(CH3)$_2$)2.7 (1H,dd,15 & 7 Hz, H-6) 3.85 (1H,dd,10 Hz & 3 Hz, H-3) 7.1–7.7 (10H, m,CPh$_2$).

6-Dimethylamino-4,4-diphenyl-3-acetoxyheptane. HCl (levo-α-acetyl Methadol. HCl)

6-Dimethylamino-4,4-diphenyl-3-heptanol (435 mg, 1.40 mmol) dissolved in ethyl acetate (10 ml) was treated with acetyl chloride (183 mg, 2.33 mmol). The mixture was refluxed for 2 hours. After allowing the solution to cool to room temperature the solvent was removed under reduced pressure to leave a white foam, this crystallised from ethyl acetate to give 6-dimethylamino-4,4-diphenyl-3-acetoxyheptane. HCl (420 mg, 79%). [α]$_D$–56°(c0.2,H$_2$O), $\delta_H$ (220 MHz;CDCl$_3$) 0.65 (3H,d,6 Hz,H-7) 0.8 (3H,t,7 Hz,H-1) 1.05 (1H,m,H-2) 1.85 (1H,m,H-2) 2.15 (3H,s, CH$_3$CO) 2.60 (6H, broad s, N(CH$_3$)$_2$) 3.0(3H,m,H-5 & H-6) 5.8 (1H,d,8 Hz, H-3) 7.45 (10H,m,CPh$_2$).

It is to be understood that the above described examples are by way of illustration only.

What is claimed is:

1. A method of preparing optically active methadones comprising the enzymatic resolution of 1-dimethyl-amino-2-propanol in the presence of ester so as to produce S-1-dimethylamino-2-propanol and R-ester of 1-dimethylamino-2-propanol, the method further comprising the conversion of one or both of the S-1-dimethylamino-2-propanol and/or R-ester of 1-dimethylamino-2-propanol to yield S(+)-methadone and/or R(−)-methadone respectively.

2. A method according to claim 1 wherein the enzymatic resolution comprises enzyme catalysed transesterification of 1-dimethylamino-2-propanol.

3. A method according to claim 1 or 2 wherein the enzymatic resolution involves the use of at least one enzyme selected from a group comprising:

Amano lipase PS (from *Pseudomonas cepacia*)

Lipase A "Amano" 6 (from *Aspergillus niger*)

Amano lipase AY (from *Candida rugosa*)

Lipase M "Amano" 10 (from *Mucor javanicus*)

Lipase M "Amano" 50 (from *Penicillium camembertii*)

Amano Lipase N conc. (from *Rhizopus niveus*)

Novozym® 435 (from *Candida antartica*)

Sigma (from Pig Liver Esterase)

Sigma (from Porcine Pancreatic Lipase).

4. A method according to claim 3 wherein the enzyme is immobilized on solid support.

5. A method according to claim 1 wherein the ester comprises vinyl acetate or vinyl propionate.

6. A method according to claim 1 wherein the S-1-dimethylamino-2-propanol and R-ester of 1-dimethylamino-2-propanol are isolated by distillation.

7. A method according to claim 1 wherein conversion of the resolved S-1-dimethylamino-2-propanol to S-(+)-methadone comprises the following steps:

(a) treatment with thionyl chloride (b) reaction of product of step (a) with diphenylacetonitrile in the presence of a base (c) Grignard reaction of product of step (b) with ethyl magnesium bromide (d) acid hydrolysis of product of step (c) to produce S-(+)-methadone.

8. A method according to claim 1 wherein step (b) is catalysed by phase transfer catalysts.

9. A method according to claim 1 wherein conversion of the resolved R-ester of 1-dimethylamino-2-propanol to R(−)-methadone comprises the following steps:

(a) treatment with thionyl chloride (b) reaction of product of step (a) with diphenylacetonitrile in the presence of a base (c) Grignard reaction of product of step (b) with ethyl magnesium bromide (d) acid hydrolysis of product of step (c) to produce R- (−) -methadone.

10. A method according to claim 1 wherein step (b) is catalysed by phase transfer catalysts.

11. A method of preparing levo-α-acetylmethadol comprising the method of preparing S-(+)-methadone according to claim 1 and converting the so prepared S-(+)-methadone to levo-α-acetyl methadol.

* * * * *